(12) United States Patent
Krill

(10) Patent No.: US 6,583,323 B2
(45) Date of Patent: *Jun. 24, 2003

(54) PROCESS FOR THE PRODUCTION OF 6-METHYLHEPTANONE

(75) Inventor: Steffen Krill, Speyer (DE)

(73) Assignee: Degussa AG, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/092,478

(22) Filed: Mar. 8, 2002

(65) Prior Publication Data

US 2002/0128517 A1 Sep. 12, 2002

(30) Foreign Application Priority Data

Mar. 8, 2001 (DE) .......................................... 101 11 071

(51) Int. Cl.$^7$ .............................................. C07C 45/72
(52) U.S. Cl. ...................................... 568/390; 568/392
(58) Field of Search ................................. 568/390, 392

(56) References Cited

U.S. PATENT DOCUMENTS

| | | |
|---|---|---|
| 3,316,303 A | 4/1967 | Mertzweiller et al. |
| 3,574,773 A | 4/1971 | Mueller et al. |
| 3,983,175 A | 9/1976 | Tamai et al. |
| 3,984,475 A | 10/1976 | Tamai et al. |
| 4,005,147 A | 1/1977 | Fischer et al. |
| 4,146,581 A | 3/1979 | Nissen et al. |
| 4,212,825 A | 7/1980 | Nissen et al. |
| 5,955,636 A | 9/1999 | Kido et al. |

FOREIGN PATENT DOCUMENTS

| | | |
|---|---|---|
| DE | 12 68 135 | 5/1968 |
| DE | 12 59 876 | 1/1970 |
| DE | 26 15 308 | 10/1977 |
| DE | 26 25 541 | 7/1980 |
| DE | 100 44 390 | 3/2002 |
| EP | 0 765 853 | 4/1997 |
| EP | 0 816 321 | 1/1998 |
| WO | WO 96/31454 | 10/1996 |

OTHER PUBLICATIONS

J. Org. Chem., vol. 32 (1967), pp. 177.
J. Org. Chem., vol. 28 (1963), pp. 45.
Bull. Soc. Chim. Fr. (1955), pp. 1586.
Wagner et al., "Synthetic Organic Chemistry", pp. 327, John Wiley & Sons, Inc. (1953).
Izv. Akad, Nauk SSSR, Ser. Khim., vol. 5 (1972), pp. 1052.
Recl. Trav. Chim. Pays Bas, vol. 28 (1909), pp. 116.
Bull. Soc. Chim. Fr., (1963), pp. 1799.
J. Org. Chem., 23, (1958), pp. 153.
Bull. Soc. Chim. Fr., (1957), pp. 112.
Nippon Kagaku Kaishi, vol. 59 (1938), pp. 224.

Primary Examiner—Johann Richter
Assistant Examiner—Sikarl A. Witherspoon
(74) Attorney, Agent, or Firm—Oblon, Spivak, McClelland, Maier & Neustadt, P.C.

(57) ABSTRACT

Methylheptanone and corresponding homologous methylketones, in particular phytone and tetrahydrogeranyl acetone, are produced by aldol condensation of isovaleraldehyde or prenal or the corresponding aldehydes with acetone in the presence of a catalyst phase, which contains an aldolizing catalyst and a heterogeneous hydrogenating catalyst.

12 Claims, No Drawings

PROCESS FOR THE PRODUCTION OF 6-METHYLHEPTANONE

BACKGROUND OF THE INVENTION

1. Field of the Invention

The invention relates to a process for the production of 6-methylheptanone or a corresponding homologous methylketone by reacting isovaleraldehyde or a corresponding longer-chain aldehyde and acetone in the presence of an alkali- or earth alkali metal-containing catalyst and a heterogeneous hydrogenating catalyst.

2. Discussion of the Background

Methylketones, in particular 6-methylheptan-2-one, tetrahydrogeranyl acetone and phytone are important intermediates and starting materials for the production of perfumes, pharmaceutical products and feedstuff additives (J. Org. Chem., 32 (1967), 177; J. Org. Chem., 28 (1963), 45; Bull. Soc. Chim. Fr. (1955), 1586), in particular of isophytol which, in turn, is a central compound of vitamin E synthesis.

The production of methylketones, in particular methylheptanone, is described in the relevant literature, various synthesis strategies being used. Thus isoamylhalides and acetic acid esters can be coupled with each other in a nucleophilic substitution reaction in the presence of stoichiometric quantities of a base (Method A). The β-ketoester that is formed as an intermediate is decarboxylated under separation of the corresponding alcohol and carbon dioxide. The process is uneconomical because it lacks atomic economy, the high quantity of waste $CO_2$ and alcohol produced and the salt load formed (Wagner et. al., "Synthetic Organic Chemistry", 327, John Wiley & Sons, Inc.).

with phosphoric acid and phosphor pentoxide (Method D) according to Bull. Soc. Chim. Fr., 1799 (1963). Both methods are unsuitable for the industrial production of methylheptanone, as stoichiometric quantities of the relevant reagents are consumed and the synthesis of the educt is a complex multi-stage process.

A large number of synthesis strategies have dealt with the accessibility of 6-methyl-5-hepten-2-one, from which the corresponding methylheptanone can be produced efficiently by catalytic hydrogenation as illustrated above (Method B). Producers of perfumes, flavorings and vitamins recognized relatively early on that 6-methyl-5-hepten-2-one is a central intermediate on the basis of which various vitamins, including vitamin E and vitamin A, carotenoids and perfumes can be produced. The main processes are explained here by way of example.

In an industrially used multi-stage process (Method E), acetone is converted in a first stage to methylbutinol in ammonia in the presence of basic catalysts. After Lindlar hydrogenation to methyl butenol, it is reacted with diketene and the intermediate formed "in situ" is converted to methylheptenone in a Caroll rearrangement (J. Org. Chem., 23, 153, (1958). Obviously, the large number of stages in the process and the use of diketene and acetylene with the associated high safety requirements, severely restrict the industrial applicability of the process.

A further process for the production of methylheptenone comprises the reaction of 2-methylpropene with formaldehyde and acetone under pressure (Method F). However, the process conditions, which require the use of high temperatures and pressures to achieve good conversions and selectivities, entail high apparatus costs and restrict the applicability of the process (DE 12 59 876, DE 12 68 135, U.S. Pat. No. 3,574,773).

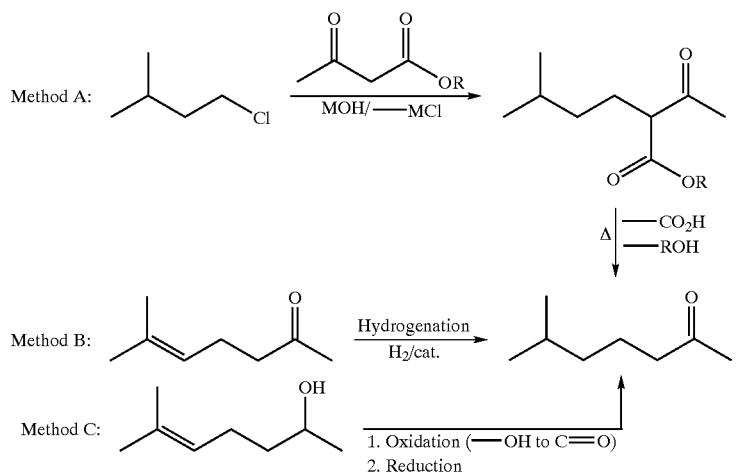

A further synthesis strategy begins initially with the production of various unsaturated methylheptanone derivatives, such as 6-methyl-5-hepten-2-one or 6-methyl-3,5-heptadien-2-one (Method B), which are hydrogenated to methylheptanone in a separate reaction step in the presence of heterogeneous catalysts (Izv. Akad. Nauk SSSR, Ser. Khim. 5 (1972), 1052). The disadvantage of this method is the cost of producing the methylheptenone and the necessity of carrying it out as a multi-stage process.

A further possibility is the oxidation of 6-methyl-5-hepten-2-ol (Method C), as disclosed in Recl. Trav. Chim. Pays Bas, 28, 116 (1909), or the treatment of the alkenol A further route to methylheptenone, which achieves the aim under moderate conditions, is a two-stage process, which has now been adapted for industrial use. In the first step, isoprene is reacted with HCl gas in the presence of a CU—I-halogenide, forming an isomer mixture of the corresponding allyl chlorides. The terminal prenyl chloride is coupled with acetone in a two-phase reaction with aqueous sodium hydroxide solution in the presence of a phase transfer catalyst (Method G). The disadvantage of this process is the stoichiometric formation of salts and moderate yields in the order of 70% (U.S. Pat. Nos. 3,983,175 and 3,984,475).

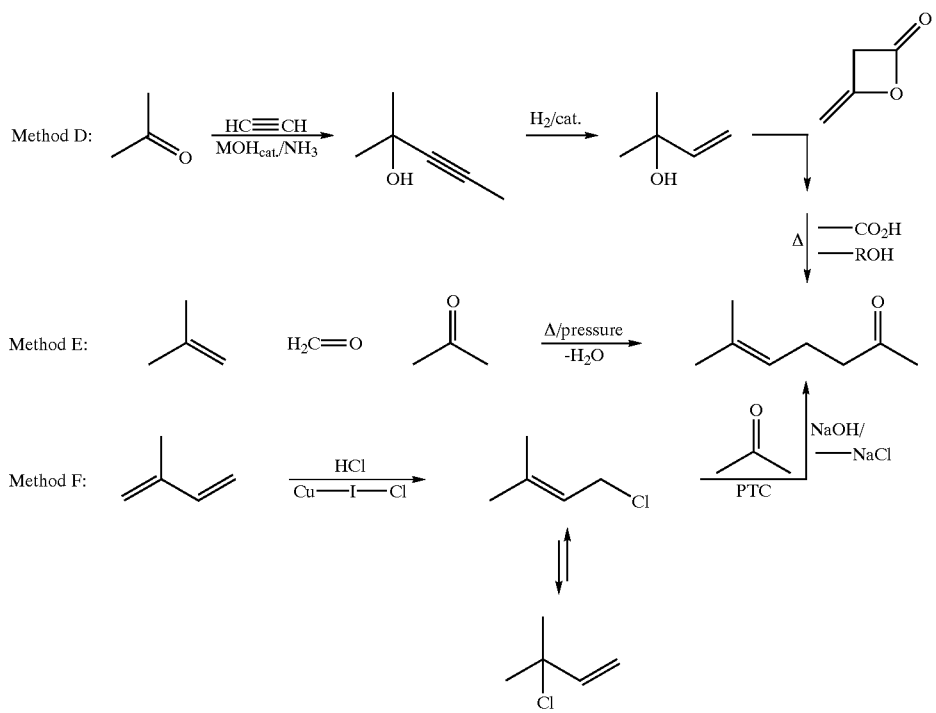

In view of the cited problems, it seems uneconomical to choose one of the stated synthesis strategies for the production of methylheptanone. In particular, the route known to 6-methylheptan-2-one via 6-methyl-5-hepten-2-one entails a high number of stages and considerable expenditure for equipment.

An alternative process is to access a double-bond isomer of 6-methyl-5-hepten-2-one, i.e. 6-methyl-3-hepten-2-one, by means of crossed aldol condensation of isovaleraldehyde and acetone at moderate temperatures in the presence of an aqueous alkali compound as a catalyst (Nippon Kagaku Kaishi, 59, 224 [1938]).

The lower reaction temperatures, which are set to achieve high selectivities, mean that the reaction also remains at the β-hydroxyketone stage (Bull. Soc. Chim. Fr., 112 [1957]).

In GB 1,246, 698 acetone and isovaleraldehyde are reacted with each other at temperatures of >200° C. and pressures of >30 bar. Only modest yields of ca. 25% are achieved and acetone is used in a molar excess of 4 equivalents. Aqueous sodium hydroxide solution is used as a catalyst for conversion. In addition, heterogeneous oxides are also disclosed as active aldolizing catalysts.

DE-OS 26 15 308 (see also U.S. Pat. No. 4,146,581) describes the use of catalytic quantities of rare earth alkali oxides and simultaneously of a heterogeneous hydrogenating catalyst (one or more metals of Group VIII of the periodic system) for crossed aldol condensation of symmetrical ketones with low aldehydes (see reaction of acetone with isovaleraldehyde, ex. 12). The reaction is carried out at higher temperatures under hydrogenating conditions (in the presence of hydrogen, preferably at 20–30 bar). According to a variant of this process, a corresponding lipophilic salt (e.g. stearate) is used as aldolizing catalyst rather than a heterogeneous rare earth alkali oxide. The disadvantage of this, substantially good, process is that to achieve good selectivities, the ketone is used in a clear excess (3–5 equivalents in relation to the aldehyde used) and aldehyde conversion is not complete. In addition to the desired methylheptanone, a considerable content of unconverted methylheptenone is also obtained from this procedure. The residence times of the heterogeneous systems used are not discussed.

DE-OS 26 25 541 (corresponds to U.S. Pat. No. 4,212, 825) also deals with a method for direct production of higher saturated ketones, in particular 6-methylheptanone, by crossed aldol condensation of acetone with 3-methyl-butanal using a heterogeneous supported contact, which contains zinc oxide as the aldolizing component and nickel, cobalt or copper as the hydrogenating component. The disadvantages of this method are incomplete conversion, unsatisfactory hydrogenation yield and by-products formed by consecutive reactions of methylheptanone with a further equivalent isovaleraldehyde (product mixture contains 2,10-dimethylundecane-6-one and unsaturated precursors). Catalyst preparation is also expensive. No details are given of the long-term activity of the catalyst.

The use of zinc oxide "per se" as an aldolizing catalyst for the production of the corresponding α,β-unsaturated ketones is disclosed in U.S. Pat. No. 4,005,147. The use of lipophilic zinc salts in the presence of a hydrogenating catalyst is disclosed in U.S. Pat. No. 3,316,303, where, in particular, the use of an unsuitable hydrogenating catalyst (sulfide of the elements Mo, Ni, W or a cobalt-carbonylizing catalyst) results in the formation of considerable quantities of the unwanted alcohol.

A further attempt to produce 6-methylheptanone is disclosed in WO 96/31454. In a two-stage process, the crossed aldol condensation of acetone with isovaleraldehyde in the presence of aqueous sodium hydroxide solution is carried out in a first stage. After obtaining a mixture containing 4-hydroxy-6-methyl-heptan-2-one, dehydration and hydrogenation follow in the presence of a catalytic quantity of Bronstedt acid and a heterogeneous precious-metal hydrogenation contact. Obviously, a multi-stage process, in particular one requiring the catalyst environment to be changed from basic to acidic, does not constitute a satisfactory solution to the existing problem. To achieve high yields, an acetone excess of 3–5 equivalents in relation to isovaleraldehyde is also used.

Another process is disclosed in U.S. Pat. No. 5,955,636, in which aldol condensation of isovaleraldehyde with acetone is carried out in the presence of an aqueous sodium hydroxide solution and a heterogeneous precious metal-hydrogenating catalyst. The hydrogenating catalyst is suspended in the acetone provided and, at the same time, both the aqueous sodium hydroxide solution and the isovaleraldehyde are dosed into this suspension at increased temperatures. The disadvantage of this process is the process costs that must be borne for the simultaneous dosing of the two solutions. After reaction, the heterogeneous hydrogenating contact must be removed by filtration, followed by phase separation, the upper phase containing the useful material 6-methylheptanone, and the lower phase the aqueous sodium hydroxide solution diluted by the reaction water. The yields that can be obtained by this process are ca. 97–98%, the yields in relation to isovaleraldehyde ca. 87%. When reproducing this process, a further disadvantage becomes apparent, namely the formation of 3-methylbutanol-1-ol as a by-product of the reaction. This by-product forms under the described conditions and only 0.5–2% in relation to the aldehyde used can be removed from the unconverted isovaleraldehyde at great expense.

After completion of the reaction, the hydrogenating catalyst is distributed between the two phases obtained and must therefore be removed by filtration before isolation of the organic useful material. The recycling or reactivation of the aqueous catalyst phase, which contains both the alkaline aldolizing catalyst and the heterogeneous hydrogenating catalyst, is not discussed.

The processes discussed in the above references do not normally seek to achieve complete conversion, as the selectivity of aldol condensation falls with increasing yield as a result of consecutive reactions of the methylheptanone formed with further equivalents of isovaleraldehyde or reactions of one of the intermediate β-hydroxyketones or methylheptenones.

A further disadvantage of the processes described is the necessity of using a high excess of acetone in order to achieve high selectivities in relation to isovaleraldehyde. However, under the given conditions, acetone tends to dimerize to mesityl oxide, which can be detected under hydrogenating conditions as methylisobutylketone. In the processes disclosed in the literature, this homoaldol condensation of acetone represents a significant secondary reaction, which considerably reduces selectivity in relation to acetone and is expressed in a high specific consumption of the ketone.

In particular, none of the proposed processes considers ways of recycling the catalyst phase, in particular the hydrogenating contact, which determines the economy of the process.

No economic process is yet known, that discloses the production of methylketones, in particular 6-methylheptan-2-one, in which satisfactory yields are produced with complete conversion (conversion >99%), and the catalyst phase containing the aldolizing catalyst and the suspended hydrogenating catalyst can be used repeatedly without loss of activity. In the context of the present invention, the term "conversion" is equivalent to the term "reaction". Furthermore, there has as yet been no successful attempt to find a satisfactory process for suppressing the unwanted formation of by-products by the hydrogenation of isovaleral to 3-methylbutanol and thus reducing the specific acetone consumption.

Application DE 100 44 390.7 discloses a process for the production of methylheptanone and corresponding homologous methylketones, in particular phytone and tetrahydrogeranyl acetone, by aldolizing isovaleraldehyde or prenal or the corresponding aldehydes with acetone in the presence of a polyvalent alcohol containing the aldolizing catalyst and the heterogeneous hydrogenating catalyst.

SUMMARY OF THE INVENTION

It is an object of the present invention to provide a process for the production of a methylketone by crossed aldol condensation of acetone with the corresponding aldehyde under hydrogenation conditions, which a.) allows the corresponding methylketone to be produced in good yields and purities with full conversion (>99%) of the aldehyde used;

b.) avoids costly processing, i.e. the simultaneous addition of both the aqueous alkali solution and the aldehyde;

c.) permits the catalyst phase containing the active hydrogenating catalyst and the alkaline aldolizing catalyst to be recycled by means of a simple industrial process;

d.) makes it possible to guarantee constantly stable yields and process conditions with repeated use of the reactivated catalyst phase;

e.) provides a stable catalyst phase, which tolerates a high level of by-products of the reaction without significant changes to the performance profile (conversion, yield, selectivity, reaction time etc.); and f.) makes it possible to suppress or reduce hydrogenation of isovaleral as an unwanted secondary reaction with the formation of 3-methylbutanol.

This and other objects have been achieved by the present invention the first embodiment of which includes a process for the production of a methylketone of formula (1)

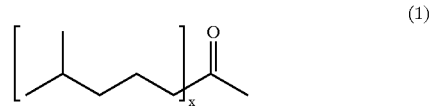

wherein x represents a number from 1–3, comprising: reacting hydrogen, acetone and an aldehyde of formula (2)

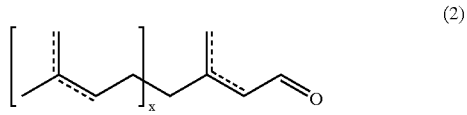

as reaction components;

wherein x represents a number from 0–2 and the broken lines each represent an olefinic double bond;

wherein said process is carried out as a 2-phase reaction and the reaction components are reacted in the presence of a catalyst suspension which contains a suspended heterogeneous hydrogenating contact and a dissolved, alkali- or earth alkali metal-containing aldolizing catalyst; and wherein the catalyst suspension is used for a further reaction cycle at the end of the 2-phase reaction.

DETAILED DESCRIPTION OF THE INVENTION

This invention is a process for the production of methylketones of the general formula (1)

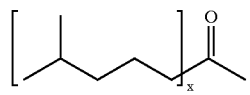
(1)

wherein x represents a number from 1 to 3 (for x=1=>6-methylheptan-2-one; for x=2=>tetrahydrogeranyl acetone; for x=3=>phytone) by reacting hydrogen, acetone and an aldehyde of the general formula (2)

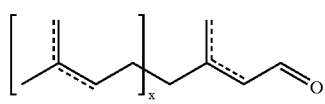
(2)

wherein x represents a number from 0 to 2 and the broken lines each represent olefinic double bonds. The components are reacted in the presence of a catalyst suspension, which contains a suspended heterogeneous hydrogenating contact and a dissolved, alkali- or earth alkali metal-containing aldolizing catalyst. The hydrogenating catalyst is used for further reaction cycles.

In particular, an improved process is disclosed for the production of asymmetrically-substituted ketones, which carry an α-methyl group, hereinafter called methylketones, by the reaction of the corresponding aldehydes with acetone under hydrogenating, dehydrating and aldolizing conditions, the educts used and the products formed having low solubility in the hydrogenating catalyst and the catalyst suspension containing the alkali- or earth alkali metal-containing dehydrating and aldolizing catalyst.

A further aspect of the invention is the two-phase reaction method, which does not use a polyvalent alcohol as a suspension agent for the heterogeneous hydrogenating catalyst and, after filtration of the hydrogenating contact, the separation of the product phase from the active catalyst phase by phase separation and recycling of the catalyst phase.

After intensive investigation, it was found that the above stated problems are solved surprisingly by a.) dissolving or suspending the alkali- or earth alkali metal-containing aldolizing catalyst and the precious metal hydrogenating catalyst powder in an aqueous phase;

b.) providing the catalyst phase together with acetone as a two-phase mixture under hydrogen in the autoclave and, while ensuring efficient stirring, pumping in the corresponding aldehyde at temperatures of 40° C. to 200° C.; and c.) once the reaction is complete and the hydrogenating contact has been separated by filtration and the desired water concentration set, optionally by reducing the reaction water, evaporating the lower phase containing the catalysts and after supplementing the spent aldolizing catalyst, reactivating it and using it for a new cycle.

The temperature in step b.) includes all values and subvalues therebetween, especially including 50, 60, 70, 80, 90, 100, 110, 120, 130, 140, 150, 160, 170, 180 and 190° C.

The following scheme outlines the reaction using the example of the acetonizing of 3-methylbutyraldehyde (isovaleraldehyde) to produce methylheptanone. The compounds in brackets are passed through as intermediates:

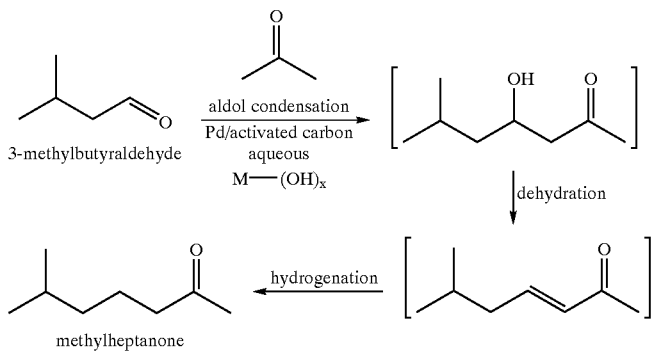

Here, catalyst phase means a phase that contains the aldolizing catalyst and the hydrogenating catalyst.

Here, by aqueous catalyst phase is meant a catalyst phase consisting of at least 80% to 99.9% by weight water and no polyvalent alcohol. The amount of water includes all values and subvalues therebetween, especially including 81, 82, 83, 84, 85, 86, 87, 88, 89, 90, 91, 92, 93, 94, 95, 96, 97, 98 and 99% by weight.

The process according to the invention facilitates processing in comparison with the process method disclosed in the prior art, as only one component must be dosed in order to achieve high selectivities.

The hydrogenation catalyst is separated off by simple technical measures such as filtration. The catalyst phase is separated from the product phase, the simplest method being decantation. The catalyst phase thus obtained contains more or less all of the reaction water formed during condensation, which considerably facilitates the processing by distillation of the organic product phase by avoiding azeotropes between water and the carbonyl compounds present. The catalyst phase contains the active hydrogenating catalyst in the form of the homogeneously-distributed suspension, and the unspent alkaline aldolizing catalyst. The water content of the catalyst phase intended for recycling can be set most simply by condensation.

Thus the process according to the invention allows an industrial one-pot concept to be used for the production of methylketones, in which the catalyst phase can be completely recycled once the reaction and phase separation have been carried out. The reaction method provides for the simple dosing of the aldehyde into the two-phase mixture of catalyst phase and acetone, which entails only negligible expenditure on process control. In this way, safe processing is still assured, as any exotherms formed are easily captured by interrupting or slowing down the dosing of the aldehyde.

Processing does not require the separation of the heterogeneous hydrogenating catalyst.

The first aspect of the invention relates to a process for the production of methylketones, in particular 6-methylheptan-2-one, by production from the corresponding carbonyl compound and acetone, characterized in that both the alkali- or earth alkali metal-containing condensation catalyst and the heterogenous hydrogenation catalyst are dissolved or suspended in an aqueous catalyst phase and the reaction is carried out in two phases. This first aspect also comprises the process method in which the aqueous catalyst phase containing the catalysts and acetone are placed in an autoclave under a moderate hydrogen pressure and the aldehyde component is dosed into the two-phase mixture of acetone and catalyst phase.

To aid comprehension, the reaction will be explained here by the example of the reaction of acetone with isovaleraldehyde to produce 6-methylheptan-2-one. The reaction takes place "in situ" via the stage of aldol condensation with the formation of the corresponding β-hydroxyketone, which is not isolated. Dehydration to 6-methylhept-3-en-2-one takes place under the reaction conditions, and this is hydrogenated selectively to the corresponding methylketone with the hydrogenation catalyst distributed homogeneously in the aqueous catalyst phase.

The molar ratio of isovaleraldehyde to acetone is not critical for the reaction and can vary over a wide range, although acetone is normally used as an excess component to achieve a high product selectivity in relation to isovaleraldehyde and a high aldehyde conversion. Good results are obtained if a molar ratio of isovaleraldehyde to acetone of 1:0.5 to 1:10, preferably 1:1 to 1:5 is used. The molar ratio of isovaleraldehyde to acetone includes all values and subvalues therebetween, especially including 1:1, 1:2, 1:3, 1:4, 1:5, 1:6, 1:7, 1:8 and 1:9.

Basic compounds are generally used as the aldolizing catalysts for crossed aldol condensation. Preferred basic compounds are for example hydroxides and carbonates of alkali- and earth alkali compounds of the elements lithium, sodium, potassium, magnesium, calcium or barium, sodium and potassium hydroxide and barium and calcium hydroxide being preferred in particular of these compounds, because they are readily available. Substantially, other components can also be used, as long as solubility in the matrix of the catalyst phase is good. The catalyst phase is produced simply by dissolving the corresponding bases, optionally while heating. In a further embodiment according to the invention, the salts are dissolved in the aqueous catalyst phase in the form of their aqueous solutions. It is also possible to use mixtures of different stoichiometries of these compounds as aldolizing catalyst.

Alcoholates of low alcohols, which have good solubility in the aqueous catalyst phase can also be used as catalysts for aldol condensation. Preferred examples are methanolates, ethanolates, isopropanolates, butanolates and corresponding branched compounds and homologues. However it should be pointed out that the use of the corresponding alcoholates has no substantial advantages over the favorable and readily available hydroxides. As water is formed by the reaction "in situ", the alcoholates convert to the corresponding metal hydroxides, with the formation of the various alcohols. Amides also catalyze the reaction effectively.

The concentration of the alkali- or earth alkali metal-containing aldolizing catalysts can be varied over a wide range. A concentration of 0.1 to 20 mol % of the corresponding bases is preferably used to achieve good space-time yields and selectivities in relation to the aldehyde used. A concentration of 0.5 to 10 mol % is particularly preferred. The concentration of the alkali- or earth alkali metal-containing aldolizing catalysts includes all values and subvalues therebetween, especially including 1, 2, 3, 4, 5, 6, 7, 8, 9, 10, 11, 12, 13, 14, 15, 16, 17, 18 and 19 mol %.

The concentration of the bases in the aqueous catalyst phase is normally set at 0.01 wt. % to 20 wt. %. A preferred range, which permits the achievement of good yields and conversions, is a concentration of 0.1 to 5 wt. %. The concentration of the bases in the aqueous catalyst phase includes all values and subvalues therebetween, especially including 0.1, 0.5, 1, 2, 3, 4, 5, 6, 7, 8, 9, 10, 11, 12, 13, 14, 15, 16,17, 18 and 19 mol %.

The reaction is normally carried out at temperatures of 20° C. to 200° C., preferably 80° C. to 140° C. to achieve high product selectivities and an adequate reaction speed. The reaction temperature includes all values and subvalues therebetween, especially including 50, 60, 70, 80, 90, 100, 110, 120, 130, 140, 150, 160, 170,180 and 190° C. It is also possible to allow the various consecutive reactions to take place at different temperature stages. Thus at the beginning of the reaction, selective crossed aldol condensation can be carried out at lower temperatures than the subsequent dehydration to α,β-unsaturated methylketone and its hydrogenation to saturated methylketone.

In the process according to the invention, the reaction can be carried out batch-wise. According to this method the aqueous catalyst phase, which contains the binary catalyst system, is provided in a pressure vessel with acetone while stirring well, the desired hydrogen pressure is set and it is brought up to the reaction temperature. The corresponding aldehyde, in particular isovaleraldehyde, is then dosed in. It is also possible to provide only the catalyst phase and to add the mixture of acetone and isovaleraldehyde. The first variant is preferred for reasons of selectivity, which we attribute to the fact that when providing acetone, the stationary relationship between acetone and isovaleraldehyde is always large enough to effectively prohibit a homoaldol condensation of isovaleraldehyde with itself.

In a further two-phase embodiment, which does entail higher apparatus costs, the aqueous catalyst phase, which contains only the suspended hydrogenation catalyst, is provided with acetone under the desired hydrogen pressure at reaction temperature and both the aldehyde and an aqueous solution of the aldolizing catalyst are dosed in.

In a further embodiment, the process is carried out continuously. Catalyst phase and educts optionally brought into contact with each other in counterflow. After reaction in the reaction zone, the phases are separated, and the aqueous catalyst phase is fed back continuously into the reactor. Before re-entry into the reactor, the spent catalyst and educts are supplemented with fresh catalyst and educts.

To carry out the two-phase reaction according to the present invention, a solvent is not necessarily required. To achieve high volume yields the process is preferably carried out without solvent. For better reaction control, in particular for better temperature management to capture reaction heat, inert solvents can be used under reaction conditions, which do not affect selectivity. Aliphatic hydrocarbons such as pentane, hexane, heptane, octane and branched homologues, or aromatic hydrocarbons such as benzene, toluene, xylene or ethers such as diethylether, dibutylether, tetrahydrofurane, dioxane, glymes, diglymes and corresponding derivatives as well as alcohols such as methanol, ethanol, propanol, butanol and branched homologues and derivatives of the said compounds for example, can be used as solvents. Higher aliphatic ketones, which have lower solubility in the glycerin phase than acetone itself, are suitable solvents according to the invention. Preferred examples of these ketones are diethylketone, methylethylketone, diisopropylketone, dibutylketone and in particular methylisobutylketone, the latter being particularly preferred as a reaction solvent, as it is a reaction by-product of homoaldol condensation of acetone.

Supported metal catalysts commercially developed and available for this purpose are preferably used as hydrogenation catalysts. Preferred metals with good selectivities and residence times are in particular palladium, platinum, rhodium and nickel, which can be used in the form of their elements, oxides and mixed oxides with other metals, or as alloys with other metals. Preferred supports are activated carbon, aluminum oxide, silicon dioxide and other commercially available supports known in the literature.

The quantities of the hydrogenation catalysts are 0.01 wt. % to 5 wt. %, particularly preferably 0.1 wt. %–1 wt. %. The quantity of the hydrogenation catalyst includes all values and subvalues therebetween, especially including 0.05, 0.1, 0.5, 1, 1.5, 2, 2.5, 3, 3.5, 4 and 4.5 wt. %.

There are no particular restrictions on the hydrogen pressure used, although good results are normally achieved at pressures of 1–40 bar. Higher pressures can also be set, but are undesirable from the point of view of the apparatus costs. A preferred pressure range is the interval of 5–20 bar. The pressure includes all values and subvalues therebetween, especially including 5, 10, 15, 20, 25, 30 and 35 bar.

A further aspect of the present invention is the processing of the two-phase reaction mixture, the conditioning of the catalyst phase before use in the new cycle being of particular importance besides product isolation and recycling of unconverted educts.

At the end of the reaction, a two-phase reaction mixture is obtained, which consists of the active catalyst phase on the one hand and the product phase on the other. The water formed by the dehydration of the β-hydroxyketone passed through "in situ" dissolves in the catalyst phase and is separated from the product by sluicing out in the catalyst phase. The suspended hydrogenation catalyst is distributed homogeneously in the aqueous catalyst phase.

The product- and catalyst phases, which form sharp phase boundaries, are separated from each other most simply by draining off the remaining product phase. The catalyst phase is composed substantially of water, the metal salt formed by Canizarro reaction, the carboxylate corresponding to the aldehyde used (if isovaleraldehyde and NaOH are used, sodium isovaleric acid forms) the aldolizing catalyst and the heterogeneous hydrogenation catalyst.

The process is characterized in that substantial quantities of by-products of the reaction, in particular the carboxylate salts arising from the Cannizarro reaction, are tolerated, with no substantial effect on selectivities and yields being observed. After supplementing the spent aldolizing bases with fresh aldolizing bases, the catalyst phase can be recycled without restrictions.

The recycled catalyst phase is characterized by its water content as well as the carboxylate salts present. The carboxylate concentration normally amounts to 0.1 to 70 wt. %, the water content is set at 0.1–50 wt. %. To achieve good yields and reduce the necessary sluicing rate, a carboxylate content of 10–30 wt. % is set. The carboxylate concentration includes all values and subvalues therebetween, especially including 0.5, 1, 5, 10, 15, 20, 25, 30, 35, 40, 45, 50, 55, 60 and 65 wt. %. The water content includes all values and subvalues therebetween, especially including 0.5, 1, 5, 10, 15, 20, 25, 30, 35, 40 and 45 wt. %. The concentration of sodium hydroxide solution in the catalyst phase, within certain limits, is not critical for the course of the reaction and is normally set at 0.01 wt. % to 20 wt. %. A preferred range is a concentration of 0.1 to 5 wt. %. The The concentration of sodium hydroxide solution in the catalyst phase includes all values and subvalues therebetween, especially including 0.05, 0.1, 0.5, 1, 5, 10 and 15 wt. %.

The organic phase of the catalyst phase consists of unconverted acetone and smaller quantities of methyl isobutylketone. The aqueous phase can be disposed of, or re-processed. The basic aldolizing catalyst is supplemented by addition without solvent, or in the form of the corresponding solutions of the bases in suitable solvents. Solvents can be low alcohols with 1–6 hydrocarbon atoms or also water.

The purity of the methylketones isolated by the process according to the invention, in particular 6-methylheptan-2-one, which can be obtained by reacting acetone with isovaleraldehyde, corresponds to the product quality required for use as an educt for the synthesis of intermediates for the synthesis of vitamin E, vitamin A and various carotinoids. The purity of the methylketones is preferably >90%, more preferably >95% and most preferably >99%.

Having generally described this invention, a further understanding can be obtained by reference to certain specific examples which are provided herein for purposes of illustration only, and are not intended to be limiting unless otherwise specified.

EXAMPLES

Example 1

Two-phase aldol condensation of isovaleraldehyde and acetone with NaOH.

250 grams (g) water were provided in a 2 liter (L) autoclave with mechanical stirrer and 6 g hydrogenating catalyst (Pd on carbon, 5 wt. %, E 101 R/W Degussa-Hüls, $H_2O$ content 53.9%) were suspended in it. 4 g NaOH (0.1 mol, 2.02 mol % in relation to isovaleraldehyde) were added to this suspension. After the NaOH had dissolved, 436 g (7.5 mol) acetone were added to this suspension. A hydrogen pressure of 15 bar was set at room temperature and with intensive stirring. The two-phase mixture was heated to 120° C. 431 g isovaleraldehyde (4.96 mol; Celanese) from a receiving flask are dosed into this mixture through a submerged coil with an HPLC pump. The molar ratio of aldehyde to acetone was thus 1:1.5.

The dosing time was 3 hours (h), the reaction temperature was maintained at 120° C.–125° C. by capturing any exotherms formed. After addition, stirring was continued for a further hour under hydrogen pressure, so that a constant pressure of 15 bar was maintained throughout the whole dosing and subsequent reaction time. Ca. 115 L hydrogen in all were taken up by the charge.

After cooling to room temperature (25° C.), the autoclave was opened and the two-phase mixture was separated. The catalyst was separated off by filtration. After phase separation an organic phase of 799.8 g and an aqueous phase of 453.3 g were obtained. The aqueous phase was condensed in a rotary evaporator up to 60° C. bath temperature at 40 mbar, the remaining aqueous catalyst phase (re-used in Example 2) had a mass of 219.6 g.

In the upper product-containing phase, the yield and concentration of by-products were determined by quantitative GC with n-dodecane as an internal standard. We detected 68.2 g methylisobutylketone (MIBK) in the organic phase, which was formed by acetone dimerization under hydrogenating conditions (equivalent to 1.36 mol acetone). Thus 18.1% of the acetone originally used had been consumed in this secondary reaction. In the aqueous phase, 2.5 wt. % 3-methylbutyric acid sodium salt was found.

Quantification showed that 609.3 g 6-methylheptanone (4.75 mol) were obtained, which corresponds to a methylheptanone yield in relation to isovaleral of 95.8%. The conversion of isovaleraldehyde was 99.9%.

Example 2

Recycling of the reactivated catalyst phase from Example 1.

The procedure was the same as in Example 1, using identical charge sizes and recycling the catalyst phase formed after phase separation (219.6 g), the unspent residual catalyst concentration (NaOH) and the quantity of sodium salt of isovaleric acid formed by catalyst consumption were analytically determined. The shortfall in the aldolizing catalyst quantity was supplemented to bring it up to the original concentration. A residual NaOH content of 0.8 wt. % (=1.75 g NaOH) and an Na-isovaleriate content of 2.5 wt. % (=5.5 g) in the catalyst phase to be recycled was obtained. This catalyst phase was reactivated with 4.5 g 50 wt. % NaOH/H$_2$O solution and supplemented with 35 g water.

With this charge the concentration of NaOH was thus also 2.02 mol % in relation to isovaleraldehyde. The hydrogenating catalyst found in the filter candle after the first charge was rinsed back onto the charge with acetone (436 g; 7.5 mol); the suspension catalyst was not supplemented with fresh catalyst. The process then continued as described in Example 1, a hydrogen uptake of 114 L H$_2$ was recorded at the end of the reaction.

At the end of the reaction, processing was carried out as described and the results were quantified. In the upper product-containing phase, the yield and concentration of by-products were determined by quantitative GC with n-dodecane as the internal standard.

In the organic phase (with a total mass of 842 g) 72.0 g MIBK were detected, formed by acetone dimerization under hydrogenating conditions (corresponds to 1.44 mol acetone). Thus 19.1% of the acetone originally used had been spent in this secondary reaction. In the aqueous phase 9.64 wt. % 3-methylbutyric acid sodium salt was found after condensation in a rotary evaporator to a mass of 145.8 g.

After quantification of the organic product phase, a 6-methylheptanone yield of 94.9% was found at an isovaleral conversion of 99.7. That corresponds to a selectivity in relation to isovaleral of 95.2%.

Example 3

Two-phase aldol condensation of isovaleraldehyde and acetone with increased NaOH concentration in relation to isovaleral.

525 g water were provided in a 2 L autoclave with mechanical stirrer and 5 g hydrogenation catalyst (Pd on carbon, 5 wt. %, E 101 R/W Degussa-Hüls, H20 content 53.9%) were suspended in it. 12 g NaOH solution (0.15 mol, 4.0 mol % in relation to isovaleraldehyde) were added to this suspension.

Once the NaOH had dissolved, 327 g (5.63 mol) acetone were added to this suspension. A hydrogen pressure of 15 bar was set at room temperature (25° C.) and with intensive stirring. The two-phase mixture was heated to 120° C. 323 g isovaleraldehyde (3.72 mol; Celanese) were dosed into this mixture from a receiving flask through a submerged coil using an HPLC pump. The molar ratio of aldehyde to acetone was thus 1:1.51.

The dosing time was 3 h, the reaction temperature was maintained at 120° C.–125° C. by capturing the exotherms formed. When addition was complete, stirring was continued for a further hour under hydrogen pressure, so that a constant pressure of 15 bar was maintained throughout the whole dosing and subsequent reaction time. A total of ca 88 L hydrogen was taken up by the charge.

After cooling to room temperature, the autoclave was opened and the two-phase mixture was separated. The catalyst was separated off by filtration. After phase separation an organic phase of 731.3 g and an aqueous phase of 725.4 g were obtained.

In the upper product-containing phase, the yield and concentration of by-products were determined by quantitative GC using n-dodecane as the internal standard. 54.9 g MIBK were detected in the organic phase, formed from acetone dimerization under hydrogenating conditions (equivalent to 1.1 mol acetone). Thus 19.5% of the acetone originally used had been consumed in this secondary reaction. 1.7 wt. % sodium salt of 3-methylbutyric acid was found in the aqueous phase.

Quantification shows that 447 g 6-methylheptanone (3.49 mol) were obtained, which corresponds to a yield of methylheptanone in relation to isovaleral of 93.8%. The conversion of isovaleraldehyde was >99.9%.

Example 4

Production of methylheptanone on the basis of prenal (=3-methyl-2-buten-1-al=dimethylacrolein) and acetone by two-phase catalysis in the presence of aqueous sodium hydroxide solution.

20 g water were provided in a 300 ml autoclave with mechanical stirrer and 0.2 g hydrogenating catalyst (Pd on carbon, 5 wt. %, E-101 R/W Degussa-Hüls, H$_2$O content 53.9%) were suspended in it. 0.2 g NaOH (5 mmol; 1.95 mol % in relation to dimethylacrolein) were added to this suspension. Once the NaOH had dissolved, 22.5 g (0.39 mol) acetone were added to this suspension. A hydrogen pressure of 9 bar was set at room temperature (25° C.) and with intensive stirring. The two-phase mixture was heated to 120° C.

21.5 g dimethylacrolein (0.255 mol; Aldrich) were dosed into this mixture from a receiving flask through a submerged coil using an HPLC pump. The molar ratio of aldehyde to acetone was thus ~1:1.5. The dosing time was 3 h, the reaction temperature was maintained at 120° C.–125° C. by capturing the exotherms formed. Once addition was complete, stirring was continued for another hour under hydrogen pressure, so that a constant pressure of 9–10 bar was maintained throughout the whole dosing and subsequent reaction time.

After cooling to room temperature the autoclave was opened and the two-phase mixture was separated. The catalyst was separated off by filtration. The aqueous phase was extracted with 2×50 ml diethylether, the organic phases were dried with Na$_2$SO$_4$. In the upper product-containing phase, yield, conversion and product selectivity in relation to prenal were determined by quantitative GC with n-dodecane as internal standard.

Quantification showed that 26.55 g 6-methylheptan-2-one (0.207 mol) were obtained in the organic phase, which corresponds to a yield of methylheptanone in relation to prenal of 92.0%. The conversion of prenal was 97.7%, product selectivity was therefore 94.2%.

German patent application 101 11 071.5, filed Mar. 8, 2001, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A process for the production of a methylketone of a formula (1)

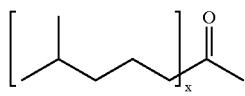
(1)

wherein x represents a number from 1–3, comprising:
reacting hydrogen, acetone and an aldehyde of formula (2)

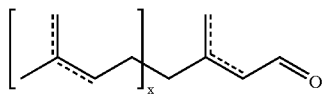
(2)

as reaction components;
wherein x represents a number from 0–2 and the broken lines each represent an olefinic double bond;
wherein said process is carried out as a 2-phase reaction and the reaction components are reacted in the presence of a catalyst suspension which contains a suspended heterogeneous hydrogenating contact and a dissolved, alkali- or earth alkali metal-containing aldolizing catalyst; and
wherein an aqueous phase of the catalyst suspension following phase separation of the aqueous phase from an organic phase, is used for a further reaction cycle at the end of the 2-phase reaction, wherein the catalyst suspension is a 2-phase mixture with acetone in the presence of hydrogen, and the aldehyde is continually dosed into it, and wherein the aldolizing catalyst is dissolved in the aqueous phase, which is also the suspension medium of the heterogeneous hydrogenating contact.

2. The process according to claim 1, wherein the hydrogenating contact and aldolizing catalyst are used in a concentration of $10^{-2}$ to 50 wt. % in relation to the aqueous phase.

3. The process according to claim 1, wherein the aldolizing catalyst is a hydroxide or carbonate of the elements lithium, sodium, potassium, magnesium, calcium or barium.

4. The process according to claim 3, wherein said aldolizing catalyst is sodium hydroxide.

5. The process according to claim 1, wherein a basic salt of an alkali- or earth alkali metal is used as the aldolizing catalyst.

6. The process according to claim 1, wherein the aldolizing catalyst is used in a quantity of 0.1–10 mol % in relation to the aldehyde used.

7. The process according to claim 1, wherein the hydrogenating contacts contains palladium or platinum.

8. The process according to claim 7, wherein said hydrogenating contact is provided on an inert support.

9. The process according to claim 7, wherein said hydrogenating contact is provided on activated carbon or aluminum oxide.

10. The process according to claim 1, wherein X in formula (1) is 1 and wherein the compound of formula (2) is either prenal or isovaleraldehyde.

11. The process according to claim 1, wherein at the end of the 2-phase reaction, a product phase is separated from the aqueous phase containing the aldolizing catalyst and the suspended hydrogenating catalyst, and after processing and supplementing of spent catalyst portions, said aqueous phase is re-used as a catalyst phase.

12. The process according to claim 1, wherein the process is carried out continuously;
wherein organic phase and catalyst suspension are brought into contact with each other in concurrent or counterflow; and
wherein, after phase separation, a product phase is separated off, while the catalyst suspension is recycled.

* * * * *